(12) United States Patent
Fukushima et al.

(10) Patent No.: US 8,023,615 B2
(45) Date of Patent: Sep. 20, 2011

(54) MEDICAL X-RAY CT APPARATUS

(75) Inventors: Harunobu Fukushima, Tokyo (JP);
Rika Hosaka, Yokohama (JP); Hitoshi Hattori, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 220 days.

(21) Appl. No.: 12/560,501

(22) Filed: Sep. 16, 2009

(65) Prior Publication Data
US 2010/0080338 A1   Apr. 1, 2010

(30) Foreign Application Priority Data

Sep. 29, 2008   (JP) ................... 2008-249951

(51) Int. Cl.
*H05G 1/06* (2006.01)
*H05G 1/04* (2006.01)
*H05G 1/02* (2006.01)
(52) U.S. Cl. .................. 378/4; 378/204; 378/210
(58) Field of Classification Search .......... 378/4, 9, 378/15, 19, 20, 193, 195, 204, 208–210; 600/407, 425–429
See application file for complete search history.

(56) References Cited

U.S. PATENT DOCUMENTS 5,805,658 A * 9/1998 Hum et al. .......... 378/4
2006/0165212 A1 * 7/2006 Sasaki et al. .......... 378/4

FOREIGN PATENT DOCUMENTS

JP   9-140697 A   6/1997
JP   9-276262 A   10/1997

* cited by examiner

*Primary Examiner* — Anastasia Midkiff
(74) *Attorney, Agent, or Firm* — Ohlandt, Greeley, Ruggiero & Perle, L.L.P.

(57) ABSTRACT

In a medical X-ray CT apparatus, a rotary portion is rotated, and a wind is produced inside the apparatus by the rotation of the rotary portion. An expanded cover portion is forced to vibrate by the wind, and noise is produced. The expanded cover portion is provided with at least one curved member including both ends. The curved member is arranged to extend along a virtual projection line obtained by geometrically projecting a virtual straight line connecting, to each other, the two ends fixed to an outer peripheral edge of an opening of the expanded cover portion onto a surface of the expanded cover portion, and the vibration of the expanded cover portion is reduced.

8 Claims, 17 Drawing Sheets

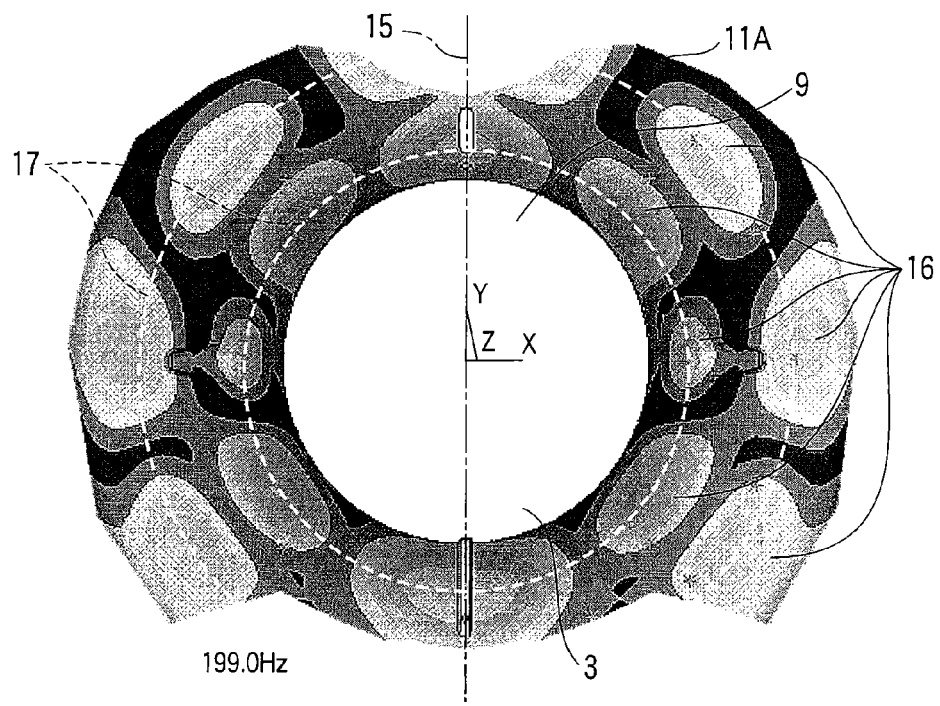
F I G. 6
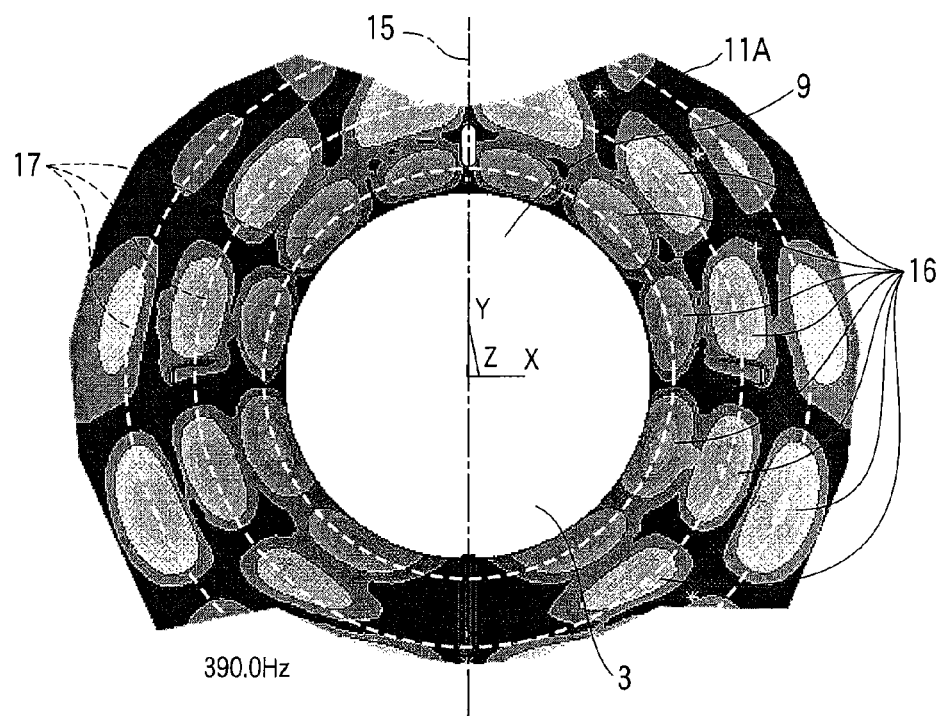
F I G. 7

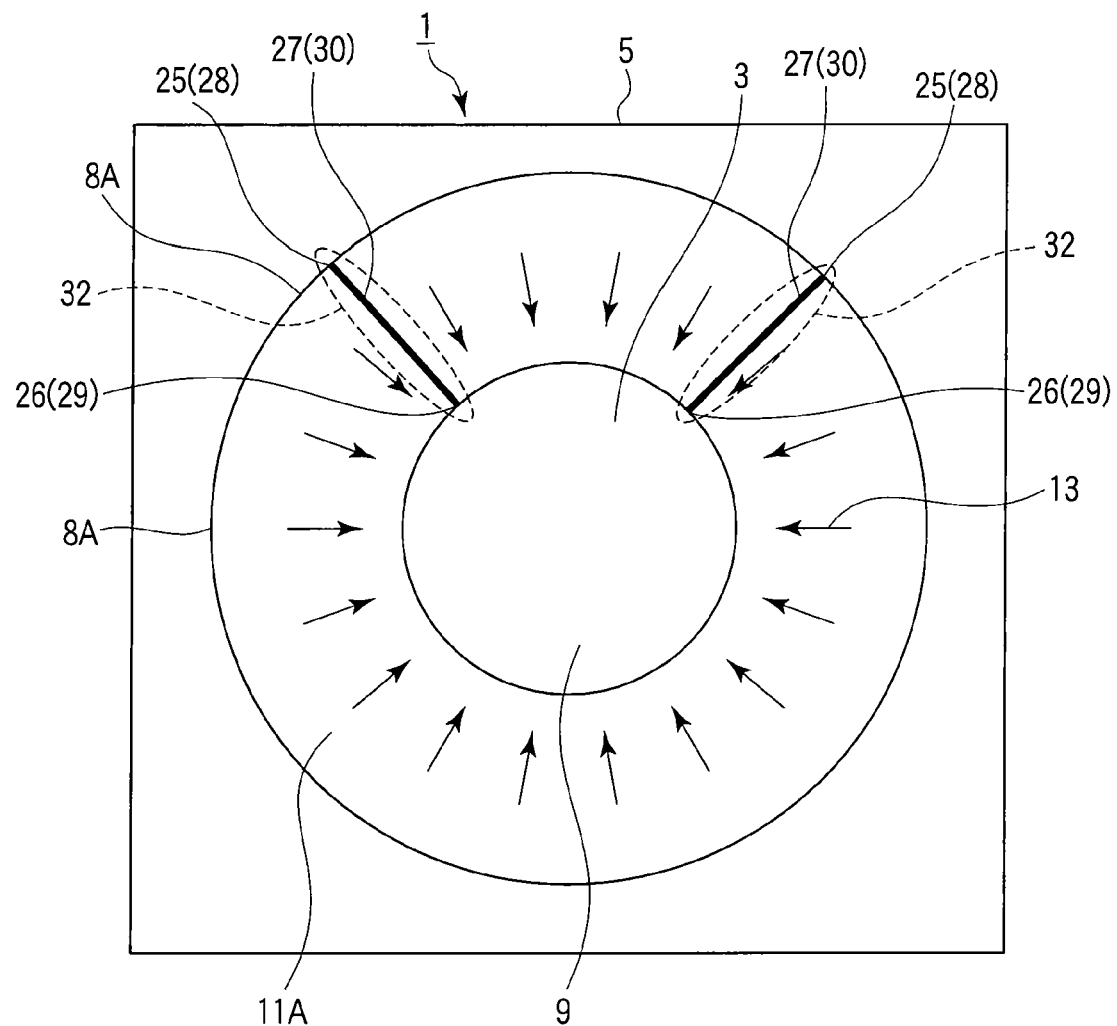
F I G. 12

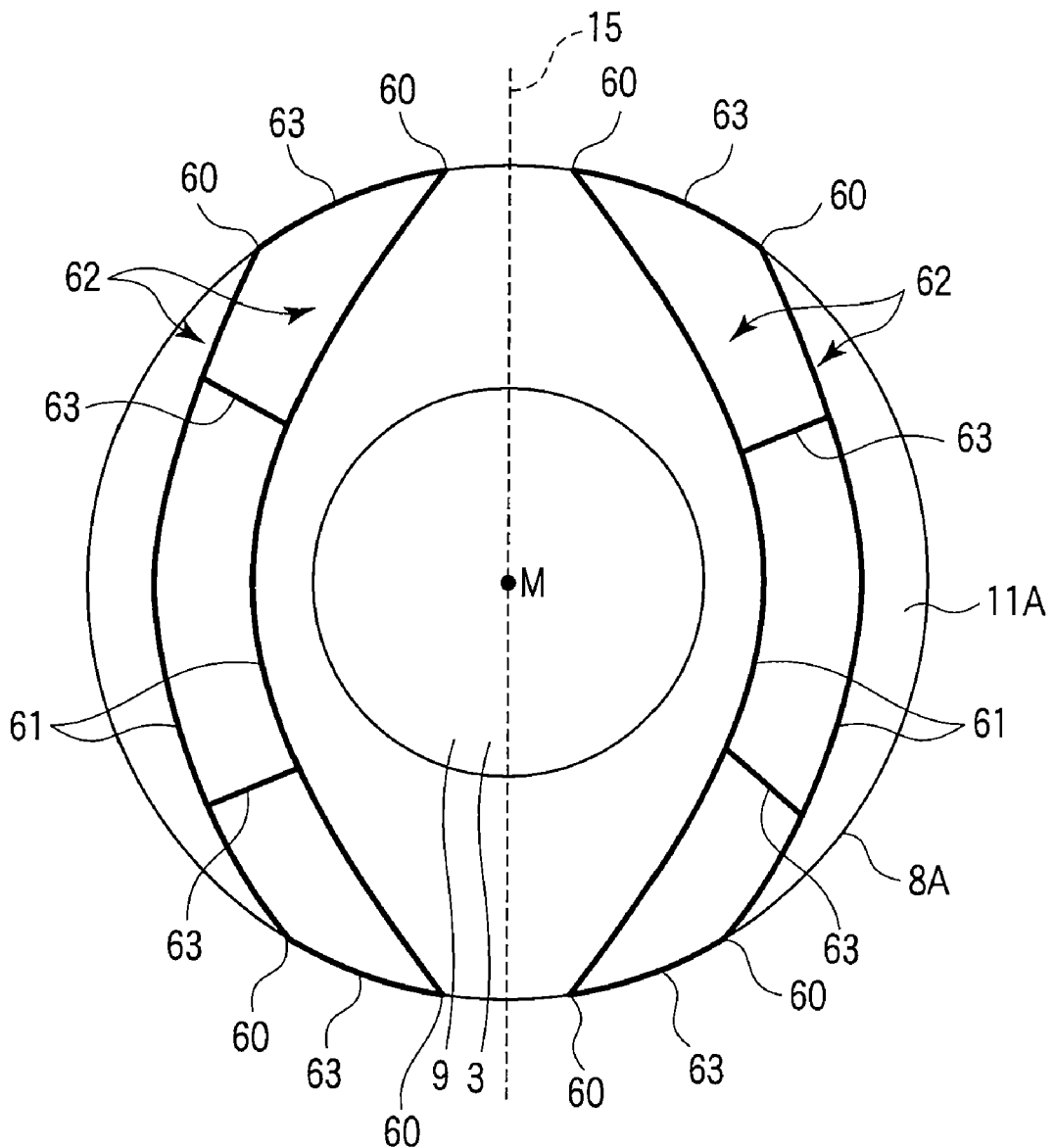
F I G. 15

MEDICAL X-RAY CT APPARATUS

CROSS-REFERENCE TO RELATED APPLICATIONS

This application is based upon and claims the benefit of priority from prior Japanese Patent Application No. 2008-249951, filed Sep. 29, 2008, the entire contents of which are incorporated herein by reference.

BACKGROUND OF THE INVENTION

1. Field of the Invention

The present invention relates to a medical X-ray computed tomography apparatus.

2. Description of the Related Art

A conventional medical X-ray CT apparatus is, as disclosed in JP-B 3587410, provided with internal devices such as X-ray tube and X-ray detector for taking tomographic images, and these internal devices are mounted on a pedestal and covered with a gantry cover, whereby a gantry of the X-ray CT apparatus is configured. This gantry cover is made of a light-weight resin material and is formed to be thin-walled in order to facilitate maintenance/checkup work. The gantry is provided with a bore into which a bed supporting a patient is inserted, and the patient lying on the bed is irradiated with X-rays to thereby acquire a tomographic image. This bore is surrounded by the gantry cover and formed in such a manner that, the bore is expanded from the central part thereof toward the opening part thereof in order to improve the operative environment at the time of subjecting the patient to tomography, diagnosis, and treatment, and give a sense of space to the patient to alleviate the mental burden on the patient.

In such a medical X-ray CT apparatus, the X-ray tube and X-ray detector are mounted on a rotary portion of the pedestal in such a manner that the X-ray tube and X-ray detector are opposite to each other across the bore. During the time of tomography imaging and rotation of the rotary portion, the patient is irradiated with X-rays emitted from the X-ray tube, and the X-rays transmitted through the patient are detected by the X-ray detector and converted into an X-ray detection signal. This X-ray detection signal is processed by a computer, and a tomographic image associated with the body of the patient is acquired.

During the tomography imaging, wind arises inside the gantry due to the rotation of the rotary portion, and the gantry cover vibrates due to the air pressure of the wind, and vibration induced noise is generated. Particularly, the expanded cover portion of the gantry cover surrounding the bore is arranged close to the rotary portion, and is therefore forced to vibrate strongly by the force of the wind. Further, the expanded cover portion is provided to surround the bore, and hence the vibration induced noise generated at the expanded cover portion is concentrated in the bore. Particularly, when the expanded cover portion is forced to vibrate at a frequency corresponding to the natural frequency thereof, the vibration of the expanded cover portion is increased, and the vibration induced noise is also increased.

In recent years, in the X-ray CT apparatus, a trend toward high-speed scanning has advanced, and the rotary portion tends to be rotated at higher speed. Consequently, the air pressure produced inside the gantry is increased, and the vibration of the expanded cover portion is also increased. As a result of this, the vibration induced noise is increased, and is perceived as intrusive. Thus, the vibration induced noise will disturb the medical practice and make the patient feel uneasy.

As a solution for reducing the vibration of the gantry cover described above, increasing the flexural rigidity of the gantry cover by adding a reinforcing material such as glass fiber into the resin material for forming the gantry cover is conceivable. However, when the constituting ratio of the reinforcing material becomes large, the formation and the manufacturing of the cover become difficult. Further, as another solution, making the flexural rigidity larger by uniformly increasing the thickness of the gantry cover is conceivable. However, this leads to an increase in weight of the gantry cover, and the labor required for transportation and assembly of the gantry cover is increased, and the efficiency at the time of maintenance/checkup is lowered.

In an X-ray CT apparatus disclosed in JP-A 09-140697 (KOKAI), a touch sensor is fitted into a fitting hole formed by substantially linear beam members on an expanded cover portion, and is fixed by mechanical connection means such as screws and the like. Although the vibration of the expanded cover portion can be reduced by fixing the touch sensor to the expanded cover portion with the mechanical connection means, a large number of fixing places must be provided, and generally it is difficult to secure sufficient fixing places. Further, providing a large number of fixing places leads to an increase in labor at the time of assembly, and lowering of the efficiency at the time of maintenance/checkup, and hence this method is impractical. Although it is also possible to reduce the vibration by increasing the cross section size of the substantially linear beam members, however, in order to reduce the vibration of expanded cover portions with large openings it is necessary to make the cross section size large, and this is difficult because the size of cross section is limited by the restriction on the outer dimensions. Further, increasing the cross section size of the beam members leads to an increase in weight of the expanded cover portion.

As described above, in the conventional medical X-ray CT apparatus, the gantry cover vibrates due to a wind generated inside the gantry by the rotation of the rotary portion, and vibration induced noise is generated, and the vibration induced noise makes the patient feel uneasy. From this point of view, a medical X-ray CT apparatus in which the vibration of the gantry cover and the intrusive vibration induced noise can be reduced without greatly increasing the weight of the gantry cover is demanded.

BRIEF SUMMARY OF THE INVENTION

According to the present invention, there is provided a medical X-ray CT apparatus for acquiring tomographic images of a patient, comprising:

internal devices which include an X-ray source for irradiating the patient with X-rays, and an X-ray detector for detecting the X-rays transmitted through the patient and outputting an X-ray detection signal;

a pedestal which has a rotary portion for mounting the internal devices and rotating the internal devices around the patient, and a support base supporting the rotary portion rotatably;

a gantry cover, having exterior and interior surfaces, configured to cover the pedestal and to form a bore having an opening through which the patient is arranged in the bore, including an expanded cover portion which is so formed as to be expanded from the inner side of the bore toward the opening and to have a peripheral edge portion on the opening side; and at least one curved member, attached on the interior surface of the expanded cover portion, has first and second ends fixed to the peripheral edge portion, includes a curved portion curved convexly toward the inside of the bore with respect to a virtual straight line connecting the first and second ends, and is configured to be extended along a curved line segment which is obtained by geometrically projecting the virtual straight line onto the expanded cover portion.

BRIEF DESCRIPTION OF THE SEVERAL VIEWS OF THE DRAWING

FIG. 6 is a view showing a result of vibration analysis of a case where vibration is carried out at the expanded cover portion shown in FIG. 5 at a frequency of 199.0 Hz.

FIG. 7 is a view showing a result of vibration analysis of a case where vibration is carried out at the expanded cover portion shown in FIG. 5 at a frequency of 390.0 Hz.

FIG. 12 is a schematic view showing a comparison between an area over which the vibration suppressing effect of the beam member extends, and an area on which the air pressure acts in the expanded cover portion shown in FIG. 9.

FIG. 15 is a schematic view showing the expanded cover portion in a case where two sets of curved members are provided in the medical X-ray CT apparatus according to the second embodiment.

DETAILED DESCRIPTION OF THE INVENTION

The X-ray CT apparatus according to various embodiments of the present invention will be described below with reference to the accompanying drawings.

First Embodiment

Figure 1:
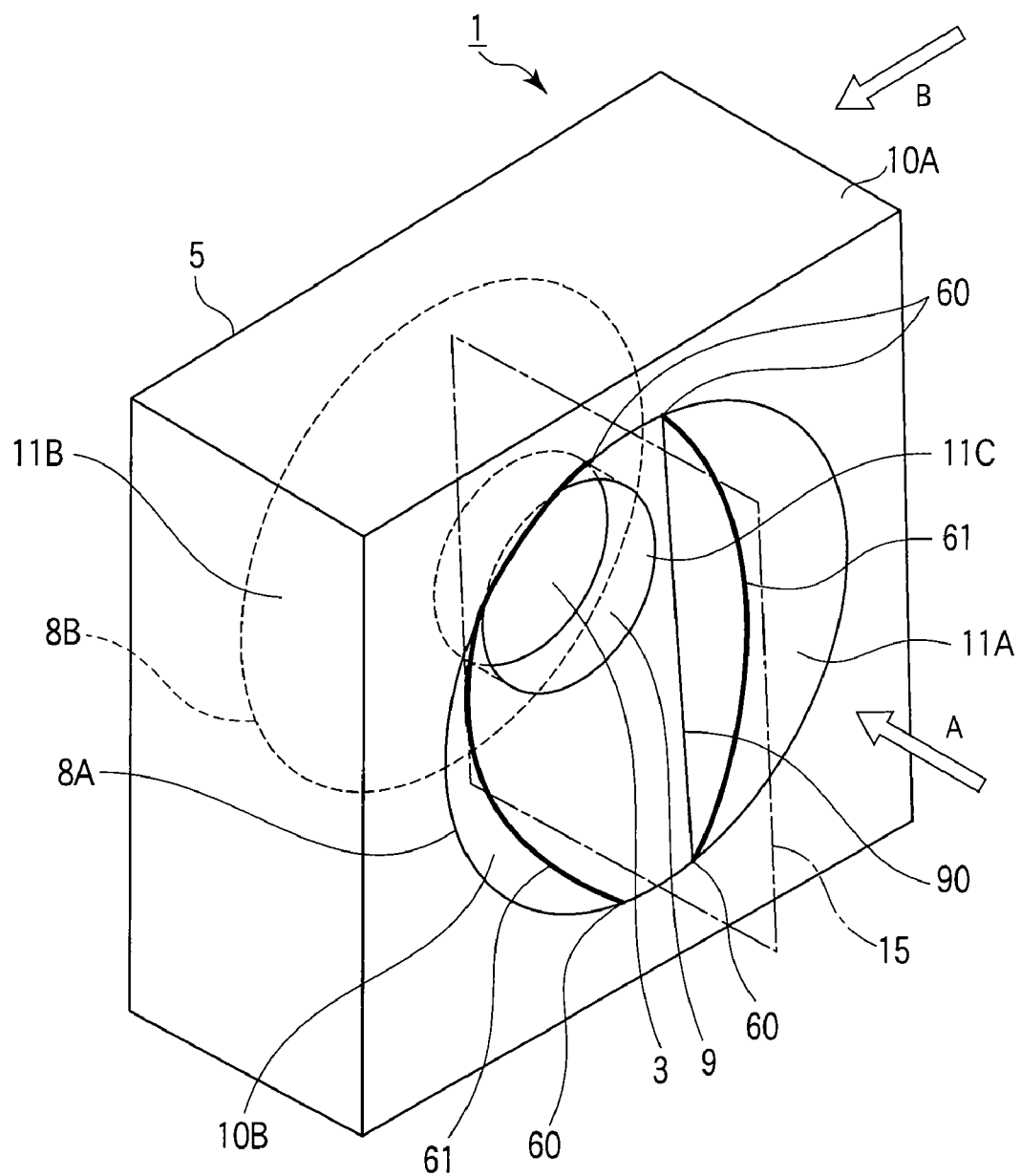
FIG. 1 is a perspective view schematically showing a medical X-ray CT apparatus according to a first embodiment of the present invention.
Figure 2:
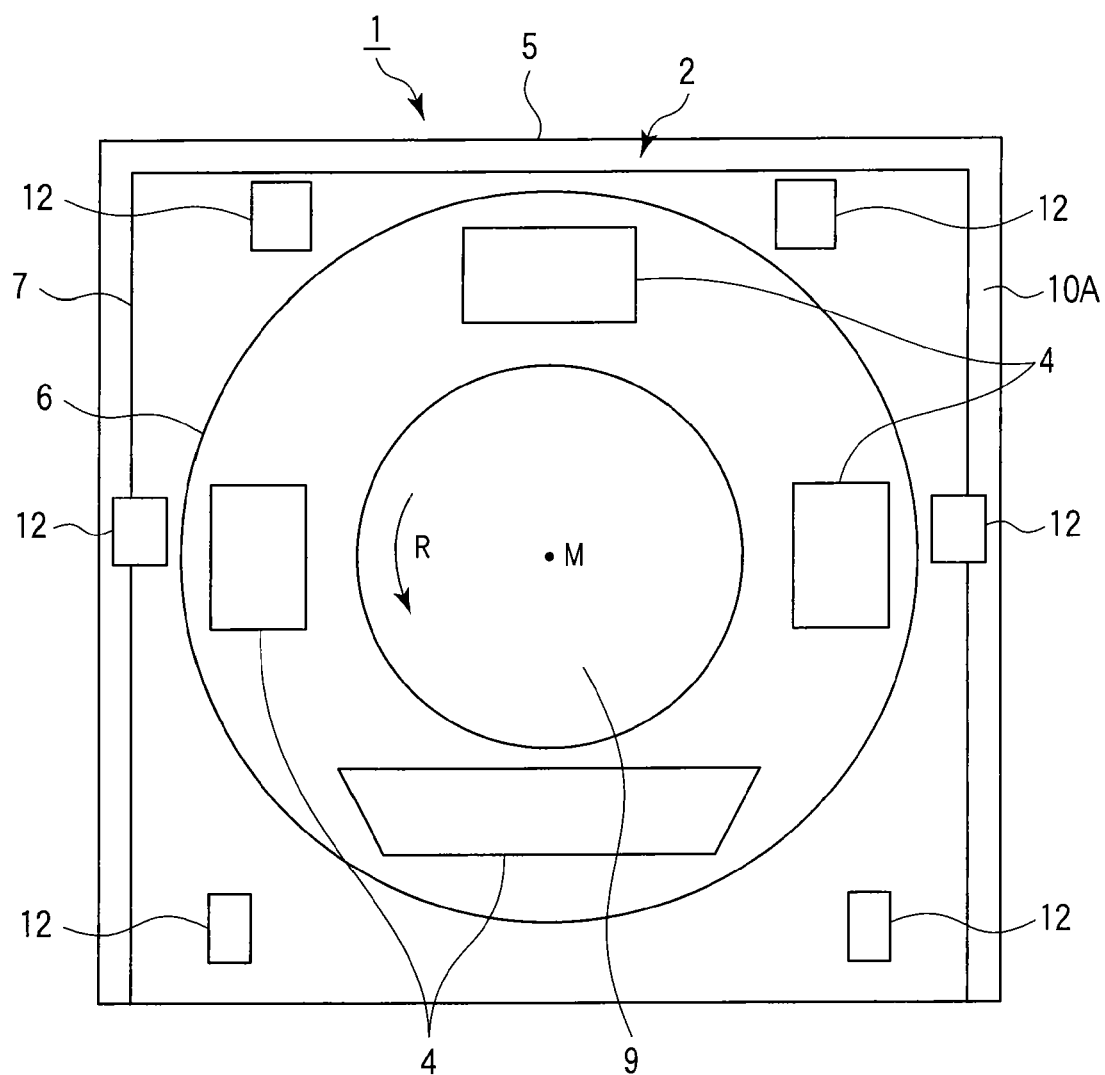
FIG. 2 is an elevation view schematically showing the medical X-ray CT apparatus shown in FIG. 1 in a seeing through manner.
Figure 3:
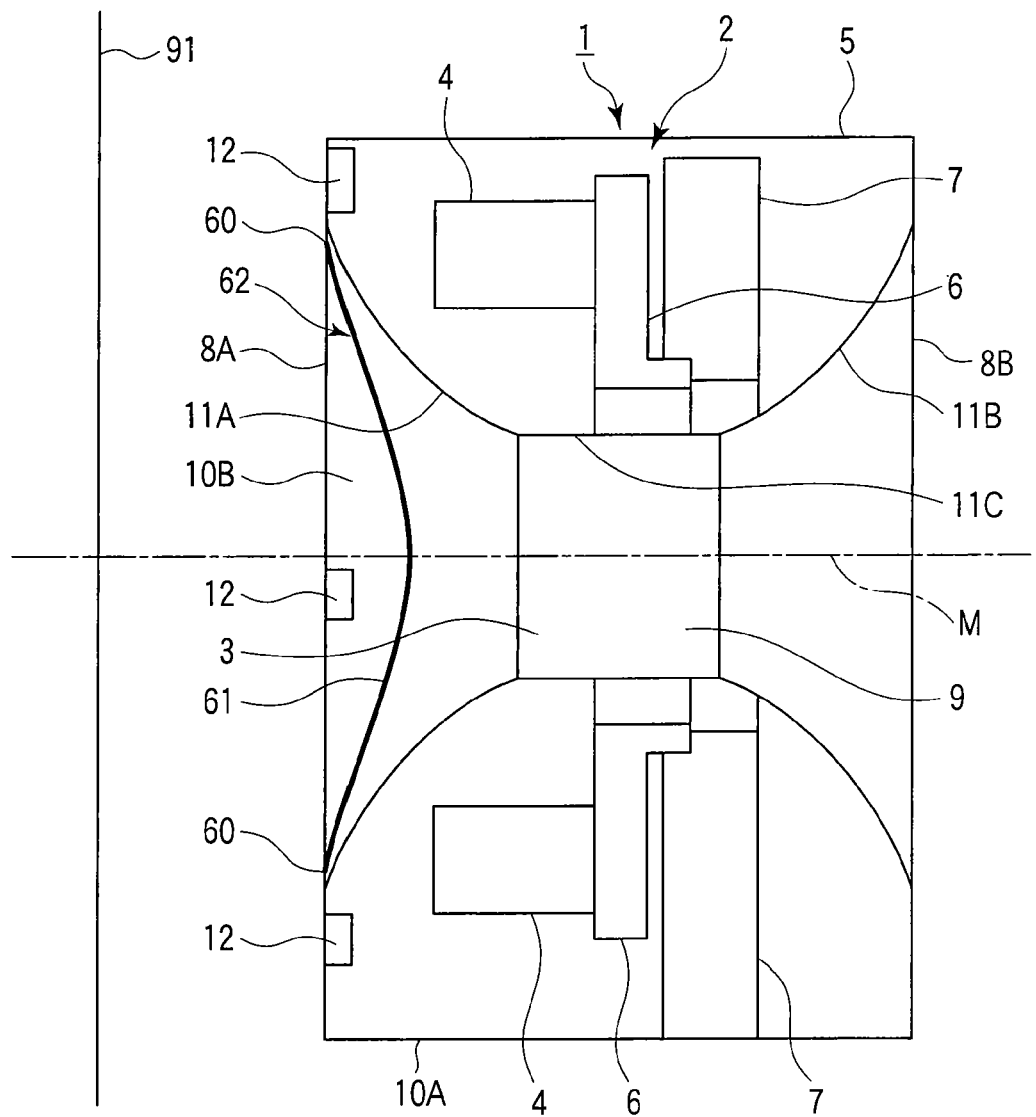
FIG. 3 is a side view schematically showing the medical X-ray CT apparatus shown in FIG. 1 in a seeing through manner.

An X-ray CT apparatus according to a first embodiment will be described below with reference to FIGS. 1 to 4B. In FIG. 1, the schematic configuration of the medical X-ray CT apparatus according to the first embodiment is shown. In FIGS. 2 and 3, the internal configuration of the medical X-ray CT apparatus shown in FIG. 1 viewed from the front (from the direction of arrow A), and that viewed from the side (from the direction of arrow B) are shown.

As shown in FIG. 2, the medical X-ray CT apparatus shown in FIG. 1 is provided with internal devices 4 in which an X-ray source such as an X-ray tube for irradiating X-rays toward a patient, and an X-ray detector for detecting the X-rays transmitted through the patient, and the like are included. These internal devices 4 are fixed to a pedestal 2, and by covering the internal devices 4 and the pedestal 2 with a gantry cover 5 a gantry 1 is formed. As shown in FIG. 1, this gantry 1 has a hollow space 9 formed to penetrate substantially the central part of the gantry 1, and the hollow space 9 is opened at openings 8A and 8B. The hollow space 9 is formed in such a manner that the hollow space 9 includes at least a part of the irradiation domain of the X-rays. Moreover, the hollow space 9 provides a bore 3 into which a bed (not shown) supporting the patient is to be inserted. As shown in FIG. 3, this bore 3 has a central hollow space which is formed into a substantially cylindrical shape with a size large enough for inserting the bed and patient, and two expanded hollow spaces. These expanded hollow spaces are formed in such a manner that the hollow spaces expand from the cylindrical central hollow space toward the opening 8A and opening 8B. Accordingly, the hollow space 9 as well as the bore 3 is formed into a shape in which two expanded hollow spaces are coupled to the two sides of the cylindrical central hollow space. The gantry 1 is provided with a computer system (not shown) serving as an image processing apparatus for processing and imaging an X-ray detection signal.

The pedestal 2 has a rotary portion 6 for rotating the internal devices 4 such as the X-ray tube, X-ray detector, and the like around the bore 3, and a support base 7 which rotatably supports the rotary portion 6. This rotary portion 6 is rotated around a rotational axis M in a predetermined direction, for example, a direction of arrow R.

As shown in FIG. 3, the gantry cover 5 includes an outer cover portion 10A for forming a box-shaped housing, and an inner cover portion 10B for separating the patient from the internal devices 4 and pedestal 2 and demarcating at least a part of the bore 3. The opening 8A of the bore 3 is formed in the front of the outer cover portion 10A, and the opening 8B of the bore 3 is formed in the rear thereof. Further, the inner cover portion 10B has an expanded cover portion 11A arranged on the opening 8A side of the bore 3 for demarcating a first expanded hollow space, and an expanded cover portion 11B arranged on the opening 8B side of the bore 3 for demarcating a second expanded hollow space, and a cylindrical cover portion 11C arranged near the center of the bore 3 for demarcating a cylindrical central hollow space. These expanded cover portions 11A and 11B are each formed into a substantially truncated cone-shape or a substantially trumpet shape, and are each formed in such a manner that the bore 3 expands curvilinearly from the vicinity of the center toward the openings 8A and 8B. Further, the cylindrical cover portion 11C is formed into a cylindrical shell-shape in order to demarcate the cylindrical central hollow space.

The gantry cover 5 has exterior and interior surfaces and is formed to be thin-walled with a light-weight resin material. The gantry cover 5 is fixed to fixing parts 12 provided in the pedestal 2 of the gantry by means of, for example, bolts or the like at an interior surface thereof. Fixing positions of the inner cover portion 10B are limited for the reasons of, avoiding contact with the rotary portion 6 and the internal devices 4, and securing the efficiency at the time of maintenance/checkup of the internal devices 4. For that purpose, the inner cover portion 10B is integrated with the peripheries of the openings 8A and 8B of the outer cover portion 10A, or is connected/fixed to the peripheries by means of bolts or the like.

Figure 4A:
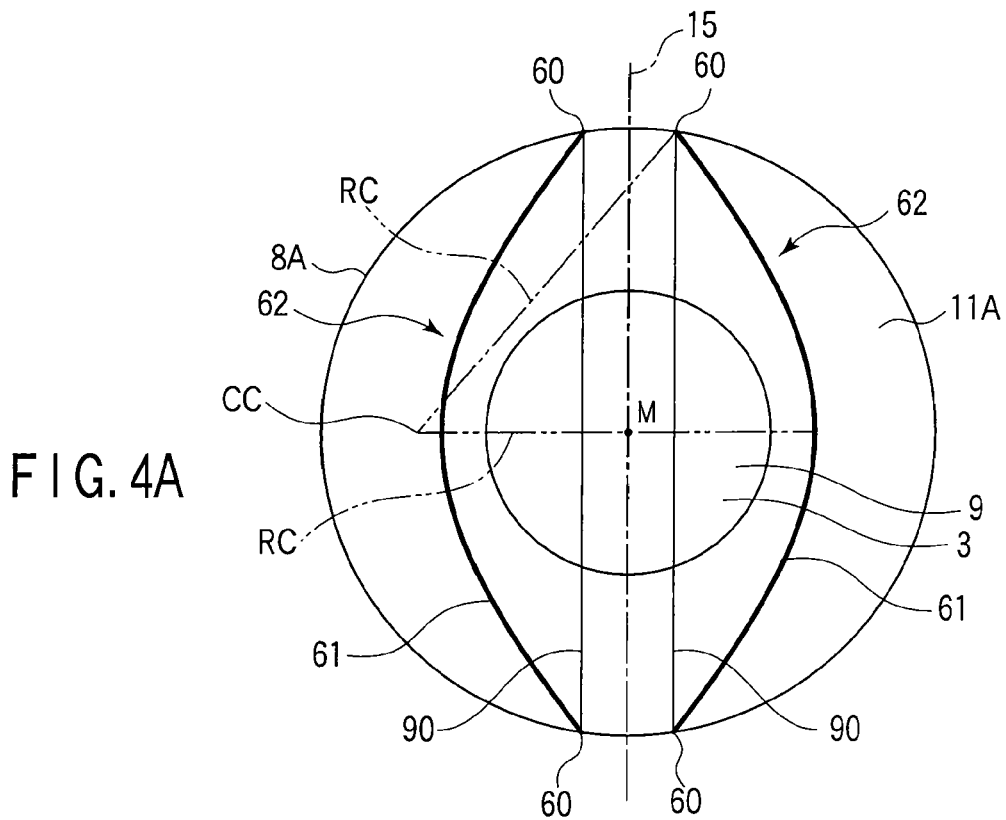
FIG. 4A is a projection view of the expanded cover portion shown in FIG. 1.

FIG. 4A shows an elevation view obtained by geometrically projecting the expanded cover portion 11A onto a virtual plane 91 which is perpendicular to the rotational axis M shown in FIG. 3. As shown in FIG. 4A, the expanded cover portion 11A is formed into a shape substantially symmetrical with respect to a reference plane 15 (corresponding to a vertical plane perpendicular to the drawing) passing through the rotational axis M, or is formed into a shape substantially symmetrical with respect to two mutually intersecting reference planes (corresponding to a vertical plane and a horizontal plane perpendicular to the drawing) passing through the rotational axis M. The expanded cover portion 11A is provided with one set of curved members 61 which have a shape substantially symmetrical with respect to one reference plane 15 (corresponding to a vertical plane). These curved members 61 are attached on the interior surface of the expanded cover portion 11A and the locations of these curved members are substantially symmetrical with respect to one reference plane 15. Hereafter, one of the curved members 61 is specifically described. The curved member 61 has two ends 60 and each end is fixed to a peripheral edge portion on the opening 8A side of the expanded cover portion 11A. The curved member 61 is arranged in such a manner that, with certain viewpoints (for geometrical projection) outside the opening 8A and a virtual straight line 90 connecting the two ends 60, the curved member 61 is extended along a virtual curved line segment which is obtained by geometrically projecting the virtual straight line 90 onto the interior surface of the expanded cover portion 11A. Furthermore, although this curved member 61 is viewed as to be extended along a planar curve in the elevation view shown in FIG. 4A, this curved member 61 is actually extended to be curved toward the cylindrical central hollow space as shown in FIG. 3. That is, this curved member 61 has a curved intermediate portion 62 which is formed to be curved convexly toward the inside of the bore 3 with respect to the virtual straight line 90 connecting the two ends 60 as shown in FIG. 3. In the elevation view shown in FIG. 4A, that is, in the projection view of the expanded cover portion 11A, the curved intermediate portion 62 is viewed as to be extended along a curved line segment having a center of curvature CC and a radius of curvature RC, the center of curvature CC is positioned on the side opposite to the curved intermediate portion 62 across the reference plane 15.

Figure 4B:
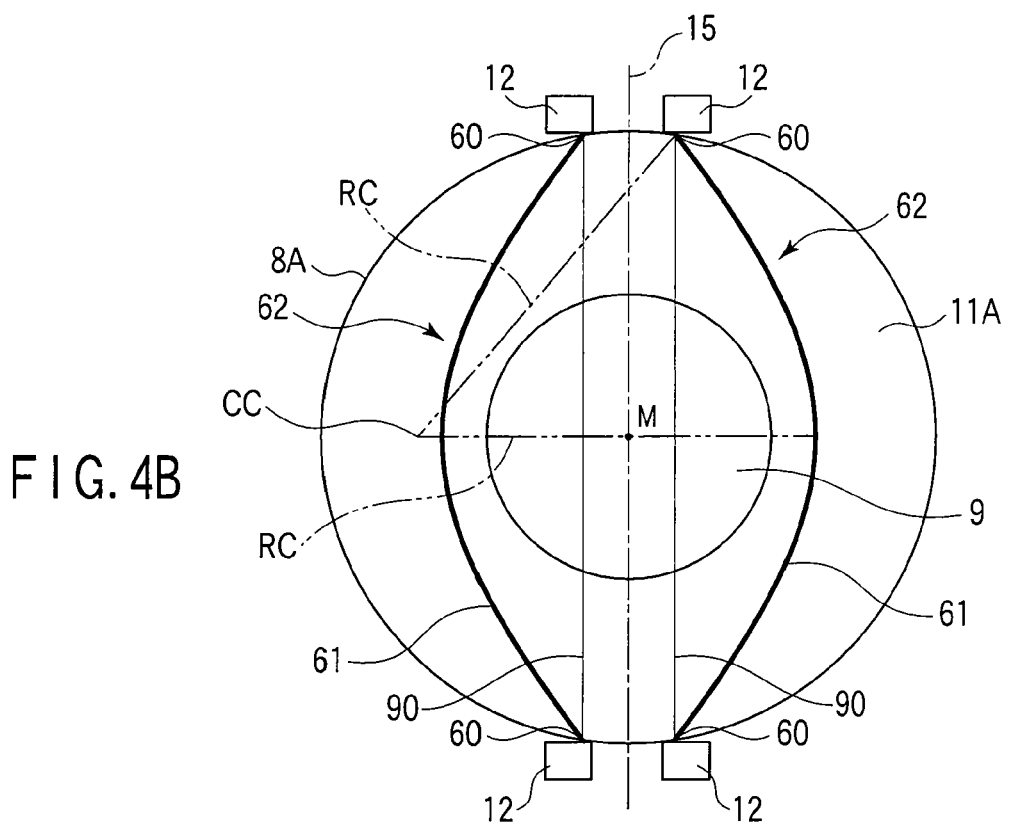
FIG. 4B is a projection view of the expanded cover portion in a case where the curved member shown in FIG. 1 is fixed to fixing parts.

Moreover, as shown in FIG. 4B, one of the ends 60 of the curved member 61, or both of the ends 60 thereof may be attached to the fixing part 12 or parts 12 to be fixed to the pedestal 2, and the curved member 61 may be provided on the interior surface of the expanded cover portion 11A as described above.

In the medical X-ray CT apparatus described above, the X-ray tube and X-ray detector are mounted on the rotary portion 6 in such a manner that the X-ray tube and X-ray detector are opposite to each other across the bore 3. While the rotary portion 6 is rotated, an X-ray beam for tomography imaging is radiated from the X-ray tube toward the patient in a form of a fan shape, and the X-ray beam transmitted through the patient's body is detected by the X-ray detector. The patient is exposed to the X-ray beam over the entire circumference thereof, and the X-rays transmitted through the patient in various directions of the patient are detected by the X-ray detector and converted into X-ray detection signals. The X-ray detection signals are processed by the computer, and a tomographic image associated with a domain of interest of the patient is acquired.

As described above, at the time of tomography imaging, the rotary portion 6 is rotated, and hence, as will be described later with reference to FIG. 5, wind is generated inside the gantry 1 by the rotation of the rotary portion 6. In the conventional medical X-ray CT apparatus, the expanded cover portions 11A and 11B are forced to vibrate by the air pressure 13 of the wind, and vibration induced noise 14 is generated at the expanded cover portions 11A and 11B. Particularly, the internal devices 4 are rotated near the expanded cover portion 11A, and hence the expanded cover portion 11A is affected more strongly by the air pressure 13 than the expanded cover portion 11B is and is forced to vibrate strongly. This vibration induced noise 14 is perceived by the patient as intrusive and makes the patient feel uneasy. In the medical X-ray CT apparatus according to the embodiment of the present invention, although the expanded cover portion 11A is forced to vibrate on account of the rotation of the rotary portion 6, the vibration of the expanded cover portion 11A is reduced by the curved members 61.

Moreover, as a variety example of the medical X-ray CT apparatus according to the first embodiment, in place of the expanded cover portion 11A the expanded cover portion 11B may be provided with the curved members 61 in the manner as described above, or both the expanded cover portions 11A and 11B may be provided with the curved members 61 in the manner as described above.

Next, a conventional medical X-ray CT apparatus provided with no curved member will be taken as a first comparative example, and the state where a rotary portion 6 is rotated, and an expanded cover portion 11A is forced to vibrate will be described below with reference to FIGS. 5 to 8.

The medical X-ray CT apparatus according to the first comparative example has a configuration substantially identical with that of the first embodiment shown in FIGS. 1 to 4A. The difference between the first comparative example and the first embodiment is that, in the medical X-ray CT apparatus according to the first comparative example an expanded cover portion 11A is not provided with a curved member 61 as a reinforcing member. In the description of the medical X-ray CT apparatus according to the first comparative example, as for constituent elements identical with those of the first embodiment, the same parts as those of the first embodiment will be denoted by the same reference symbols as those shown in FIGS. 1 to 4, and the description of them will be omitted.

Figure 5:
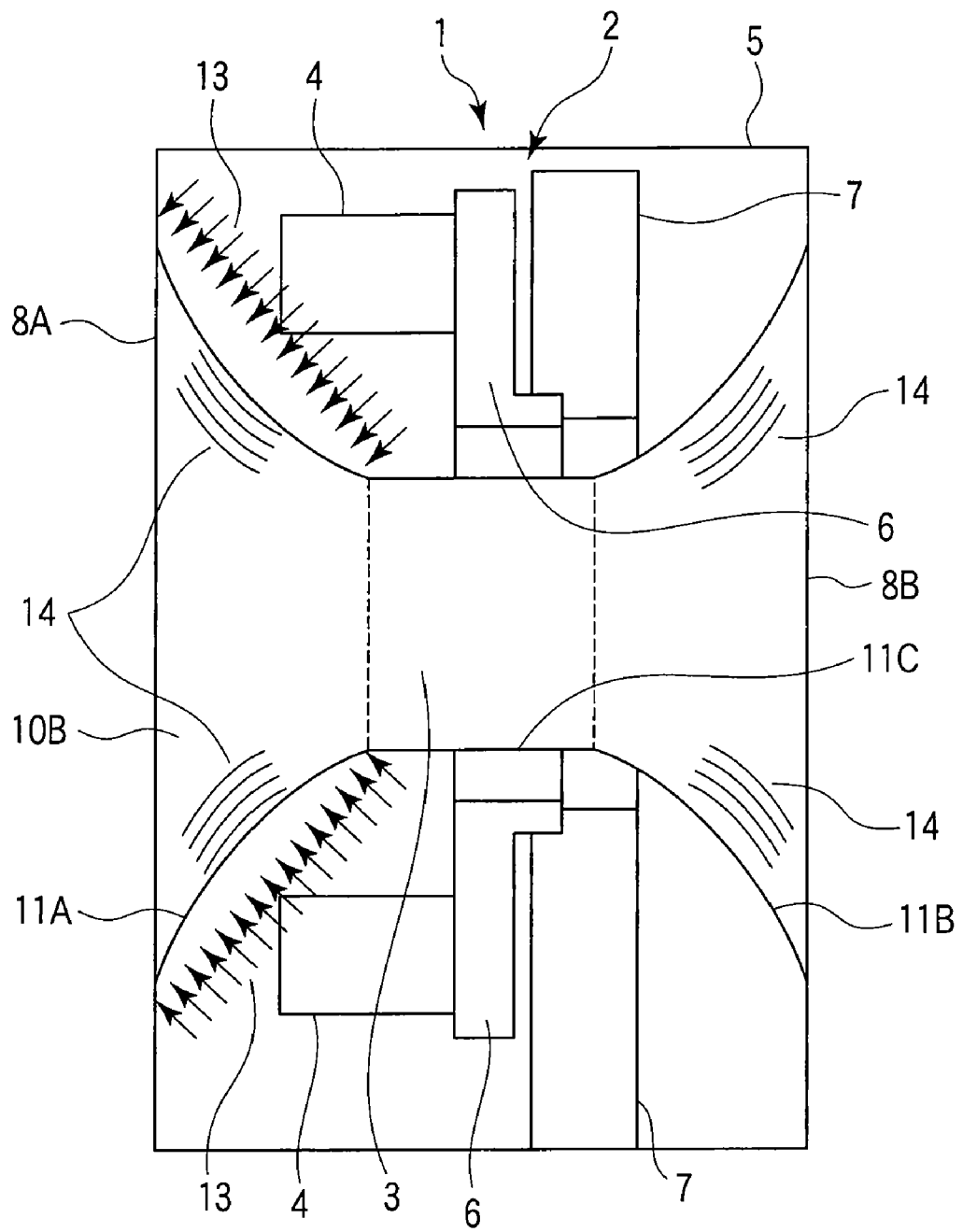
FIG. 5 is a view schematically showing a medical X-ray CT apparatus according to a first comparative example, and is a schematic view for explaining the behavior of the gantry cover in producing vibration induced noise.

FIG. 5 schematically shows the state where vibration induced noise 14 is generated from expanded cover portions 11A and 11B by a wind caused by the rotation of a rotary portion 6. In the medical X-ray CT apparatus according to the first comparative example, a wind is generated in a gantry 1 by the rotation of the rotary portion 6, and the gantry cover 5 is forced to vibrate by the air pressure 13 indicated by arrow marks as shown in FIG. 5. Due to the vibration of the gantry cover 5, the vibration induced noise 14 is generated from the gantry cover 5 as indicated by the wave marks. Particularly, because the expanded cover portion 11A is formed to be thin-walled with a light-weight resin material, i.e., is formed to be of small flexural rigidity, and is provided in close proximity to the rotary portion 6 and internal devices 4, as a result, the expanded cover portion 11A is forced to vibrate more strongly than other parts. Further, the expanded cover portion 11A is provided to surround a bore 3, and hence the vibration induced noise 14 generated at the expanded cover portion is concentrated in the bore 3.

Figure 8:
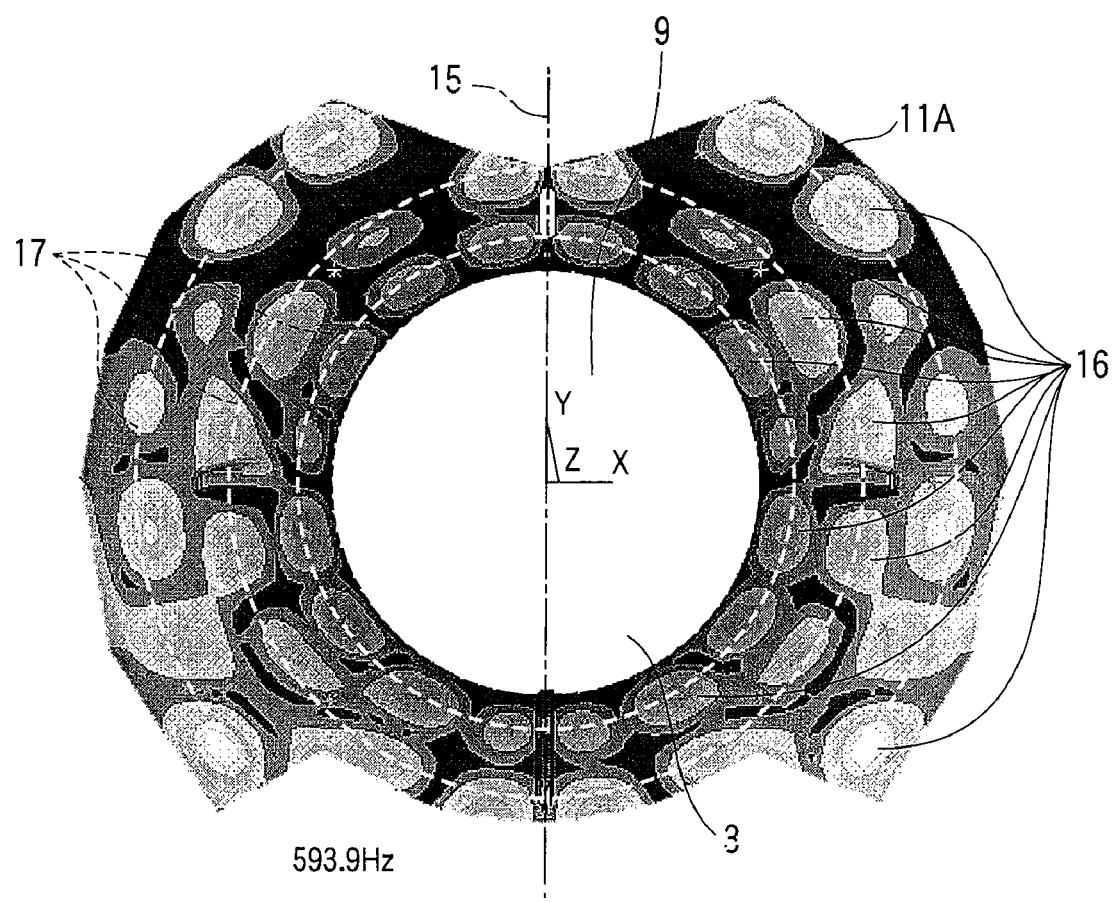
FIG. 8 is a view showing a result of vibration analysis of a case where vibration is carried out at the expanded cover portion shown in FIG. 5 at a frequency of 593.9 Hz.

When the gantry cover 5 is forced to vibrate at a frequency coinciding with each natural frequency of the gantry cover 5, a natural vibration mode is excited, and the gantry cover 5 is forced to vibrate more strongly, and the vibration induced noise 14 is increased. The inventors of the present invention have carried out the vibration analyses about the expanded cover portion 11A in the case where the expanded cover portion 11A is forced to vibrate in the natural vibration mode. In FIGS. 6, 7, and 8, results of vibration analyses in the cases where the expanded cover portion 11A is forced to vibrate at vibration frequencies of 199.0, 390.0, and 593.9 Hz are shown. These results are the vibrations of the expanded cover portion 11A viewed from the front (corresponds to the arrow A direction shown in FIG. 1) of the medical X-ray CT apparatus. The shape of the expanded cover portion 11A used in the vibration analyses is substantially symmetrical with respect to the reference plane 15. As shown in FIGS. 6, 7, and 8, it can be seen that, antinodes (parts at which vibration is large) 16 of the natural vibration mode are distributed to surround the hollow space 9 in the form of a plurality of substantial annuli, i.e., distributed substantially in a concentric circles form. Further, it can also be seen that as the natural frequency becomes high, the numbers of antinodes 16, and annuli 17 increase. Accordingly, in the expanded cover portion 11A, antinodes 16 distributed on an annulus 17 having a larger radius are positioned in the vicinity of the opening 8A, and antinodes 16 distributed on an annulus 17 having a smaller radius are positioned on the cylindrical cover portion 11C side. The occurrence positions of antinodes 16 of each natural vibration mode are different from that of other natural vibration modes. In addition, the positions of antinodes 16 distribute over a wide domain of the expanded cover portion 11A.

As described above, in the first comparative example, each natural vibration mode has an annular distribution pattern of antinodes 16 different from that of other natural vibration modes, and a large number of antinodes 16 present in a wide frequency range, and vibration induced noise is generated by the vibration of the expanded cover portion 11A and concentrated in the bore 3.

In the first embodiment, the one set of curved members 61 is provided on and fixed to the expanded cover portion 11A, and the vibration of the expanded cover portion 11A is reduced by the curved members 61.

Next, a medical X-ray CT apparatus according to a second comparative example will be described below with reference to FIGS. 9A to 12. In FIGS. 9A to 12, the same parts as those shown in FIGS. 1 to 4 will be denoted by the same reference symbols as those shown in FIGS. 1 to 4, and description of them will be omitted.

Figure 9A:
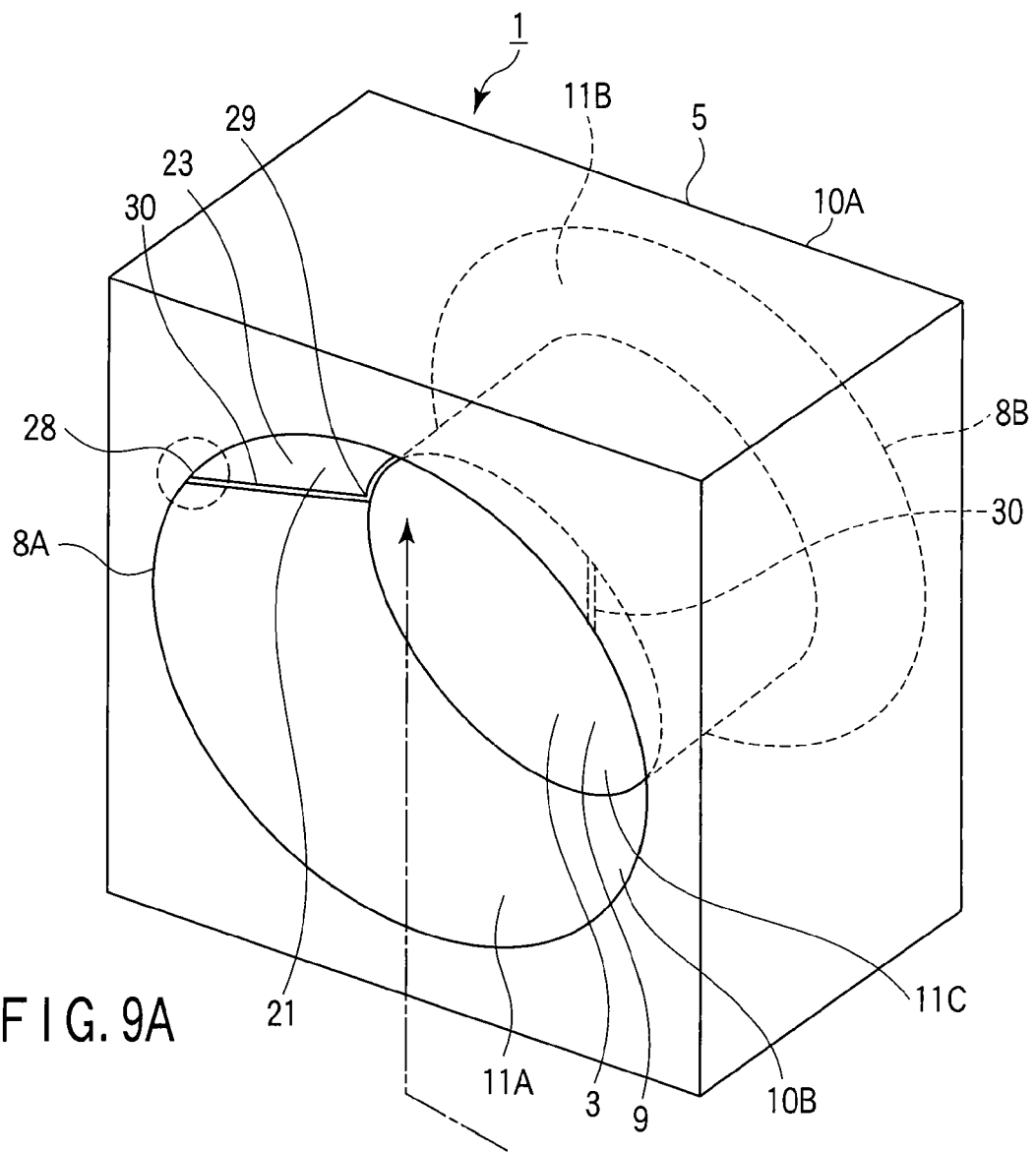
FIG. 9A is a perspective view schematically showing a medical X-ray CT apparatus according to a second comparative example.
Figure 9B:
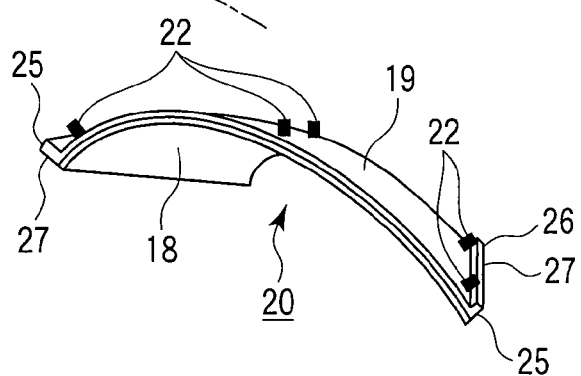
FIG. 9B is a perspective view showing a touch sensor assembly detached from the expanded cover portion shown in FIG. 9A.

FIG. 9A shows the schematic configuration of a medical X-ray CT apparatus according to the second comparative example, and FIG. 9B shows a touch sensor assembly 20 detached from an expanded cover portion 11A shown in FIG. 9A.

As shown in FIG. 9B, this touch sensor assembly 20 is provided with a touch sensor 18 which has flexibility and is provided to avoid the contact between a patient and gantry cover 5 at the time of so-called tilt scanning to be carried out by tilting the gantry 1. The touch sensor 18 is attached to a base 19 formed in such a manner that the base 19 is provided with a curved surface identical with a curved surface of an expanded cover portion 11A by using a member provided with rigidity, for example, fiber-reinforced plastics. The touch sensor 18 is attached to the base 19 to thereby form a touch sensor assembly 20, and the touch sensor assembly 20 is attached to the expanded cover portion 11A. In this manner, the touch sensor 18 is attached to the base 19 to form the touch sensor assembly 20, whereby it becomes easy to handle the touch sensor 18, and attach the touch sensor 18 to the expanded cover portion 11A. In the touch sensor assembly 20, beam members 27 are provided at both ends of the base 19, and each member 27 has a substantially linear shape and is formed between an end 25 on the opening 8A side and end 26 on the cylindrical cover portion 11C side.

Figure 10:
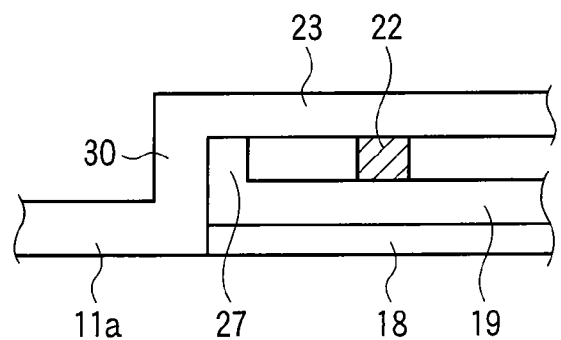
FIG. 10 is a cross-sectional view schematically showing a beam member of the fitting hole shown in FIG. 9.

The touch sensor assembly 20 is fitted into a fitting hole 21 provided on the expanded cover portion 11A, and is attached to the expanded cover portion 11A in such a manner that the surface of the expanded cover portion 11A on the hollow space 9 side becomes flat without unevenness. This fitting hole 21 is formed as a hole with a bottom or a through-hole. FIG. 10 schematically shows a cross section of the expanded cover portion 11A in a state where the touch sensor assembly 20 is attached to the expanded cover portion 11A in the case where the fitting hole 21 is a hole with a bottom. As shown in FIG. 10, when the fitting hole 21 is a hole with a bottom, the touch sensor assembly 20 is fixed to several positions of the bottom surface 23 of the fitting hole 21 by attachable/detachable mechanical coupling means, for example, screws 22 or the like provided on the base 19. Such a fitting hole 21 has substantially linear beam members 30 which are respectively provided between an end 28 positioned on the opening 8A side of the expanded cover portion 11A, and end 29 positioned on the cylindrical cover portion 11C side of the expanded cover portion 11A. Further, when the fitting hole 21 is a through-hole, a frame portion (not shown) is provided inside the gantry 1, and the touch sensor assembly 20 is fixed to a plurality of positions of the frame portion by attachable/detachable mechanical coupling means, for example, screws 22 or the like provided on the base 19.

The expanded cover portions 11A and 11B, bottom surface 23 of the fitting hole 21, and touch sensor assembly 20 according to the second comparative example are acted on and forced to vibrate by the wind produced by the rotation of the rotary portion 6, and vibration induced noise is produced. As described above, the touch sensor assembly 20 is normally fixed to the expanded cover portion 11A by point restraining means such as screws 22. In order to reduce the vibration of the expanded cover portion 11A and touch sensor assembly 20 in the natural vibration mode, it is necessary to provide a large number of fixing positions. However, it is considered to be difficult to secure fixing positions, because the expanded cover portion 11A is arranged in close proximity to the internal devices 4, and rotary portion 6. Further, it is also considered to be impractical to provide a large number of fixing positions, because the work for attaching the touch sensor assembly 20 to the expanded cover portion 11A becomes complicated, and an increase of labor, and lowering of the efficiency at the time of maintenance/checkup are brought about.

Figure 11:
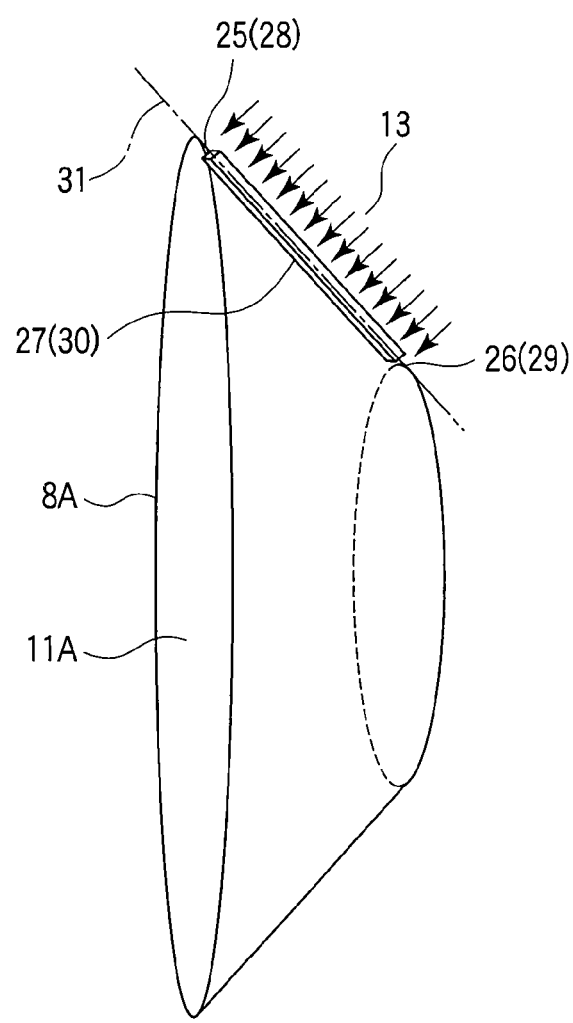
FIG. 11 is a schematic view showing the state where the air pressure caused by the rotation of the rotary portion acts on the expanded cover portion shown in FIG. 9.

FIG. 11 schematically shows the state where the air pressure 13 indicated by arrows acts on the expanded cover portion 11A. As shown in FIG. 11, the air pressure 13 acts on the expanded cover portion 11A at substantially right angles thereto, i.e., at substantially right angles to an axis line 31 of the beam member 27 or 30, and hence the action of the air pressure 13 is mainly opposed by the flexural rigidity of the beam member 27 or 30. Accordingly, by making the sectional size of the beam member 27 or 30 large, i.e., by making the moment of inertia of area large, the flexural rigidity is made large, and the bending of the beam member 27 or 30 is made small, whereby it is possible to suppress the vibration of the expanded cover portion 11A. However, when the opening 8A of the expanded cover portion 11A is large, a long beam member 27 or 30 becomes necessary. When the beam member 27 or 30 becomes long, it is necessary to make the sectional size of the beam member 27 or 30 larger in order to suppress the vibration of the expanded cover portion 11A. As a result of this, the height of the beam member 27 or 30 is increased, and there is the possibility of the beam member 27 or 30 being unable to be applied due to the limitation of the allowable size or the like. Further, the beam member 27 is formed between the end 25 and end 26 through the shortest route, and the beam member 30 is also formed between the end 28 and end 29 of the expanded cover portion 11A through the shortest route. As shown in FIG. 12, the vibration suppressing effect is limited to a neighborhood area 32 of the area in which the beam member 27 and 30 are arranged. Accordingly, it is necessary to provide the expanded cover portion 11A with a large number of beam members. In this case, the weight of the expanded cover portion 11A is increased, and the problem of lowering of the efficiency at the time of maintenance/checkup is caused.

As described above, in the second comparative example, the expanded cover portion 11A is reinforced by the substantially linear beam members 27 provided at both the ends of the touch sensor assembly 20, and the substantially linear beam members 30 for forming the fitting hole 21. However, by only the two beam members 27 and two beam members 30, it is difficult to reduce the vibration induced noise 14 occurring in the wide domain of the expanded cover portion 11A. Accordingly, in order to suppress the vibration of the expanded cover portion 11A, it is necessary to arrange a large number of beam members 27 and 30. However, arranging a large number of beam members 27 and 30 leads to an increase in weight of the gantry cover 5, and the problem that the efficiency at the time of maintenance/checkup is lowered is caused, this being impractical.

In comparison with the second comparative example, in the medical X-ray CT apparatus according to the first embodiment, the expanded cover portion 11A is provided with one set of curved members 61 arranged substantially symmetrical with respect to the reference plane 15 including the rotational axis M, and halving the expanded cover portion 11A substantially symmetrical. Each curved member 61 includes the curved intermediate portion 62, and both the ends 60 thereof are fixed to the peripheral edge portion of the expanded cover portion 11A on the opening 8A side. In the projection of the expanded cover portion 11A onto a plane 91 perpendicular to the rotational axis M, each curved member 61 is fixed to the expanded cover portion 11A in such a manner that the center of curvature CC of the curved intermediate portion 62 is positioned on the side opposite to the curved intermediate portion 62 across the reference plane 15. By the curved members 61, components of the air pressure 13 acting on the surface of the expanded cover portion 11A parallel with and perpendicular to the rotational axis M are simultaneously supported, and the vibration of the expanded cover portion 11A is reduced. Further, movements of antinodes 16 in the natural vibration mode of the expanded cover portion 11A are restrained by each other through the curved members 61, and the amplitude in the natural vibration mode is suppressed. As a result of this, the vibration induced noise 14 of the expanded cover portion 11A is reduced in the wide frequency range.

Figure 13:
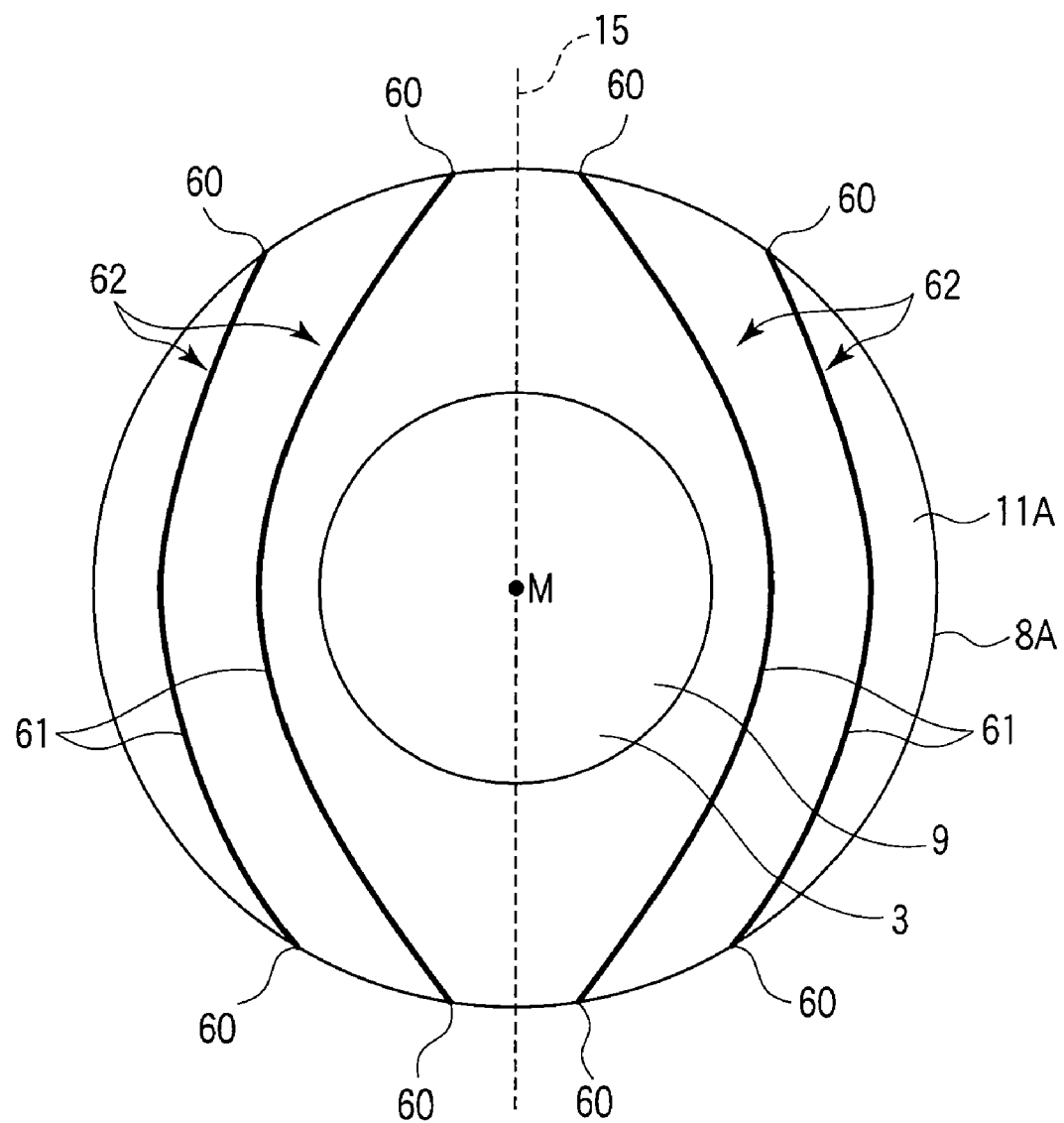
FIG. 13 is a schematic view showing the expanded cover portion in a case where two sets of curved members are provided in the medical X-ray CT apparatus according to the first embodiment.

As a variety example of the X-ray CT apparatus shown in FIG. 1, the expanded cover portion 11A may be provided with two sets of curved members 61 as shown in FIG. 13. As has already been described previously, it is desirable that one or more sets of curved members 61 be provided symmetrically on the expanded cover portion 11A. In the variety example of the X-ray CT apparatus shown in FIG. 13, two sets of curved members 61 are provided on the expanded cover portion 11A symmetrically with respect to the reference plane 15. In this variety example of the X-ray CT apparatus, by being provided with a plurality of sets of curved members 61, it is possible to further suppress the vibration of the expanded cover portion 11A.

It should be noted that it is sufficient if at least one curved member 61 is provided, and it is clearly stated here that an effect sufficient to reduce the vibration of the expanded cover portion 11A can be obtained even in the case where only one curved member 61 is provided. Further, the provision location of the curved member is not limited to the interior surface of the expanded cover portion 11A, and the curved member 61 may be configured by reinforcing the material at the locations where a curved member is to be provided on the expanded cover portion 11A.

Second Embodiment

Next, a medical X-ray CT apparatus according to a second embodiment will be described below with reference to FIG. 14. In the medical X-ray CT apparatus shown in FIG. 14, the configuration other than the configuration of an expanded cover portion 11A is identical with the medical X-ray CT apparatus according to the first embodiment, and hence the same parts as those shown in FIGS. 1 to 4 will be denoted by the same reference symbols as those shown in FIGS. 1 to 4, and description of them will be omitted.

In the medical X-ray CT apparatus according to the second embodiment, an expanded cover portion 11A is provided with, in addition to curved members 61, one or more connection members 63 for connecting each curved member 61 to the peripheral edge portion of the expanded cover portion 11A. Each curved member 61 is connected to the peripheral edge portion of the expanded cover portion 11A by the connection members 63, whereby it is possible to further reduce the vibration of the expanded cover portion 11A.

Figure 14:
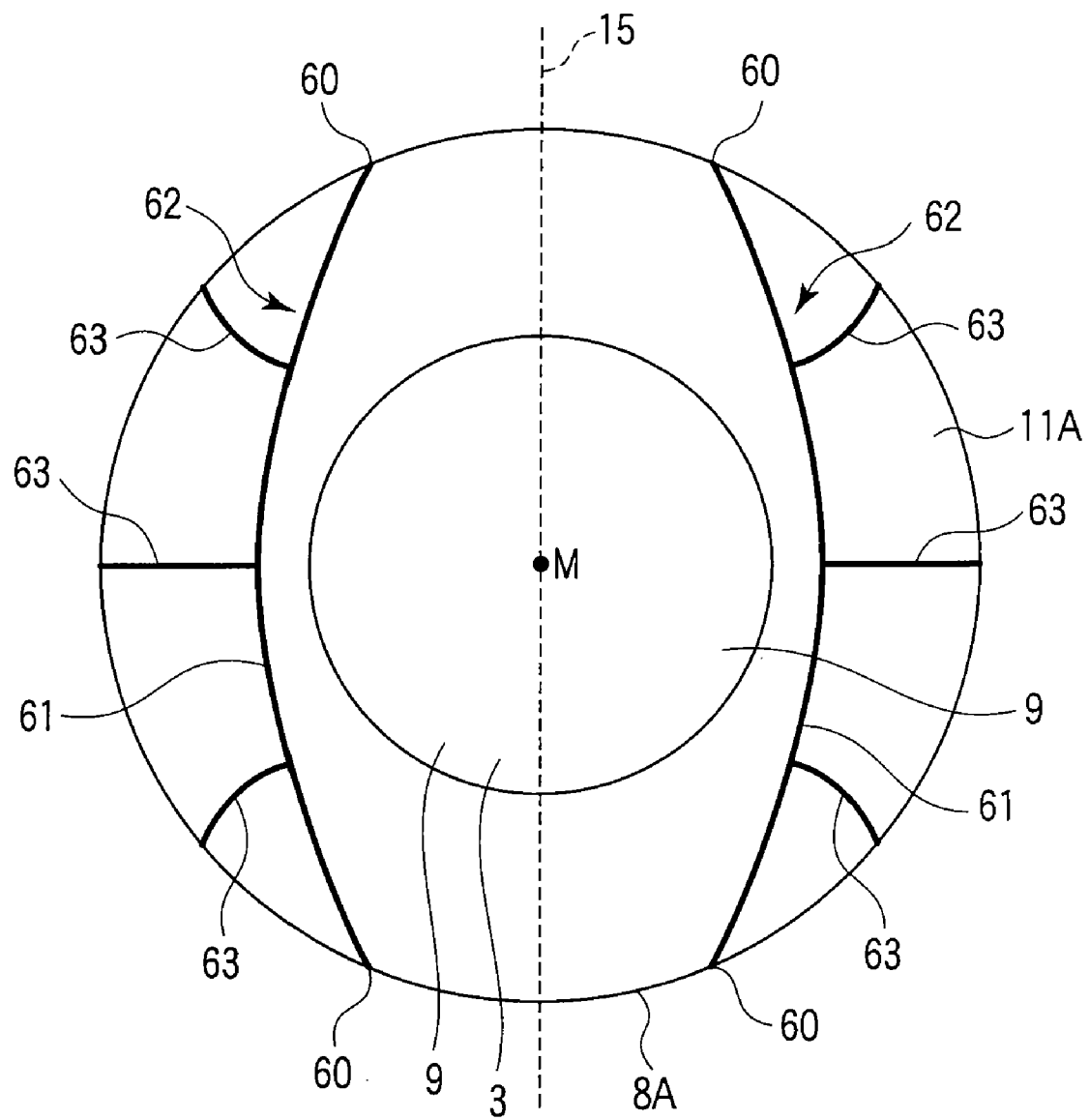
FIG. 14 is a schematic view showing an expanded cover portion of a medical X-ray CT apparatus according to a second embodiment.

More specifically, as shown in FIG. 14, the expanded cover portion 11A is provided with a set of curved members 61 as in the medical X-ray CT apparatus according to the first embodiment, and a plurality of, for example, three connection members 63 for each curved member 61 are attached on the interior surface of the expanded cover portion 11A so as to be extended from an intermediate portion of each curved member 61 to peripheral edge portion of the expanded cover portion 11A. That is, the plurality of connection members 63 arranged on the interior surface of the expanded cover portion 11A are formed to connect each curved member 61 and the peripheral edge portion of the expanded cover portion 11A, and the expanded cover portion 11A is reinforced, whereby it is possible to further reduce the vibration of the expanded cover portion 11A.

Moreover, when the expanded cover portion 11A is provided with a plurality of sets of curved members 61, the curved members 61 may be connected to each other by the connection members 63. For example, when the expanded cover portion 11A is provided with first and second sets of curved members 61 in accordance with the method specified in the first embodiment, and the connection members 63 may be provided to connect the curved member 61 in the first set to the curved member 61 in the second set as shown in FIG. 15. Further, the connection members 63 may be provided along the peripheral edge portion of the expanded cover portion 11A to connect the curved member 61 in the first set to the curved member 61 in the second set. Further, the provision location of the curved members 61 and connection members 63 is not limited to the interior surface of the expanded cover portion 11A, and the curved members 61 and connection members 63 may be configured by reinforcing the material at the locations where curved members and connection members are to be provided on the expanded cover portion 11A.

As described above, in the medical X-ray CT apparatus according to the second embodiment, the expanded cover portion 11A is reinforced by the curved members 61 and connection members 63, whereby it is possible to restrain the expanded cover portion 11A from vibrating.

Next, the inventors of the present invention have verified the vibration suppression effect of the expanded cover portion 11A by the configurations of the first and second embodiments by carrying out the following numerical experiment through a simulation.

Figure 16:
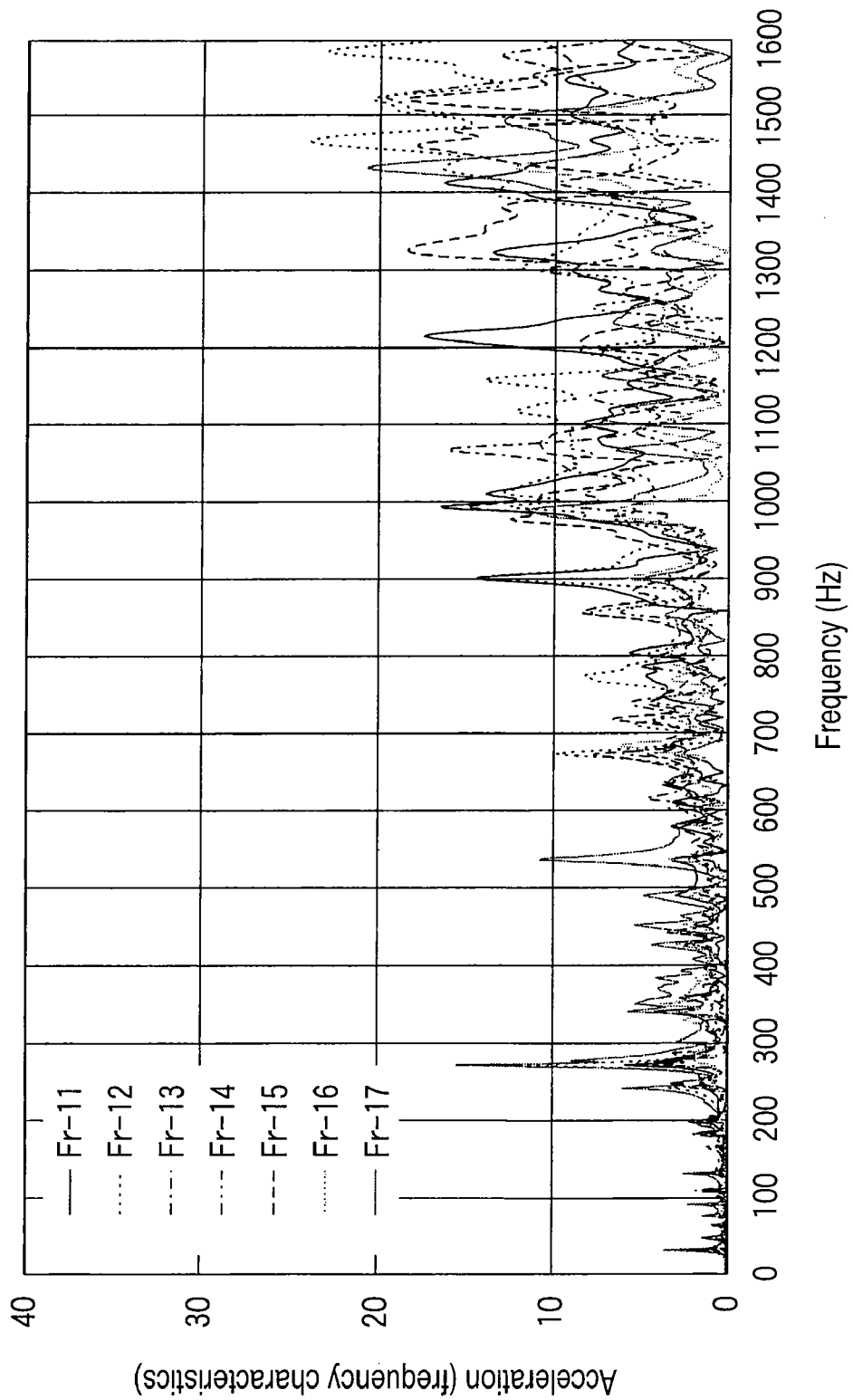
FIG. 16 is a graph showing the frequency characteristics of acceleration due to the vibration of the expanded cover portion of the first comparative example.
Figure 17:
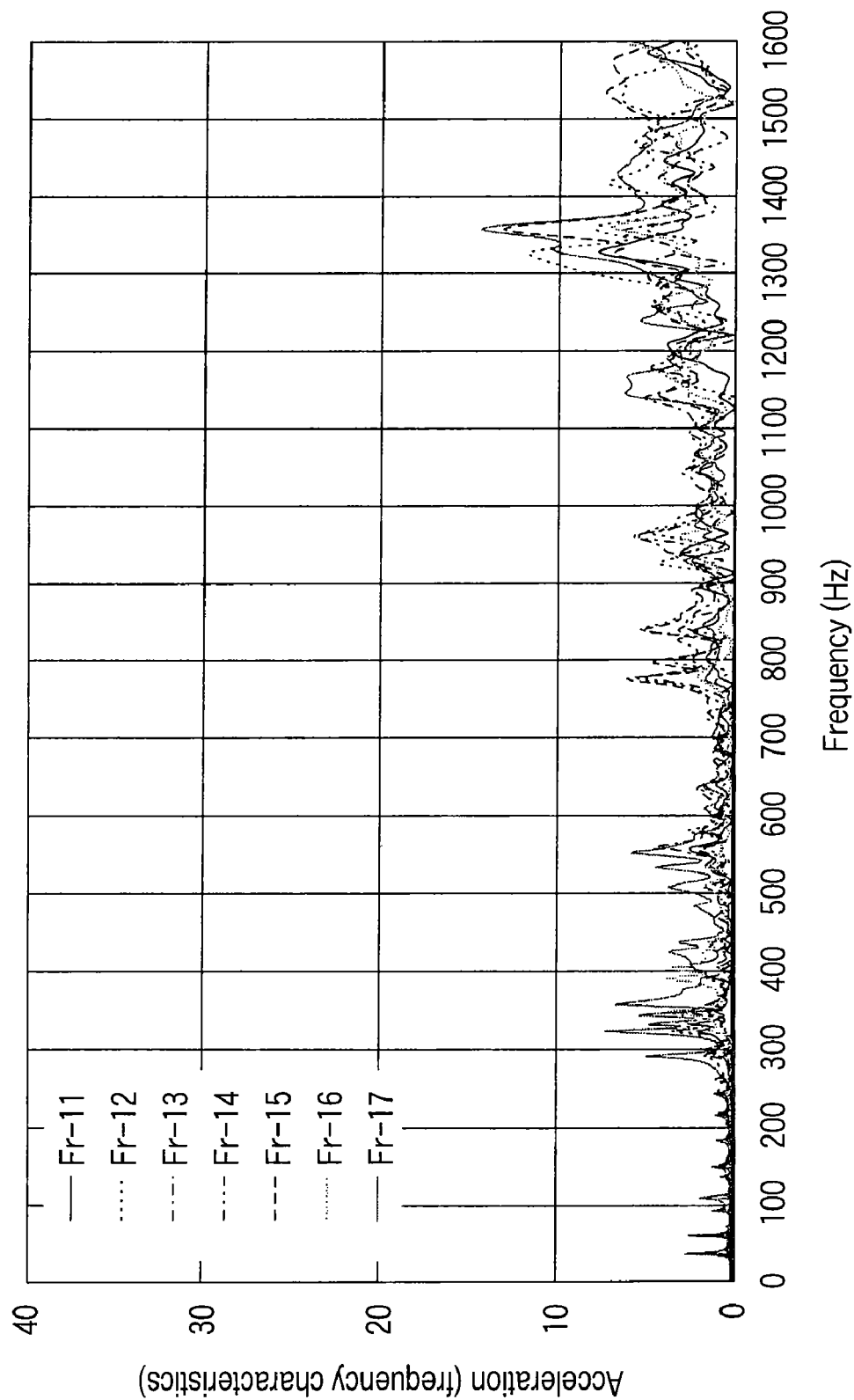
FIG. 17 is a graph showing the frequency characteristics of acceleration due to the vibration of the expanded cover portion of the first comparative example in a case where the thickness of the expanded cover portion is increased.

In FIGS. 16 to 19, frequency characteristics of acceleration due to vibration at each of observation points (not shown) Fr-11 to Fr-17 of the expanded cover portion 11A are shown. In each experiment, the expanded cover portion 11A is formed in such a manner that the thickness thereof is substantially uniform. FIG. 16 shows a result of a first experiment carried out on the medical X-ray CT apparatus according to the first comparative example. The configuration of the medical X-ray CT apparatus in the first experiment is called the reference case. FIG. 17 shows a result of a second experiment carried out by increasing the thickness of the expanded cover portion 11A in the reference case to 1.5 times. In this second experiment, although the vibration of the expanded cover portion 11A is reduced as a whole as compared with the first experiment, the weight of the gantry cover 5 (part associated with maintenance/checkup including the expanded cover portion 11A) is increased by about 26% as compared with the reference case.

Figure 18:
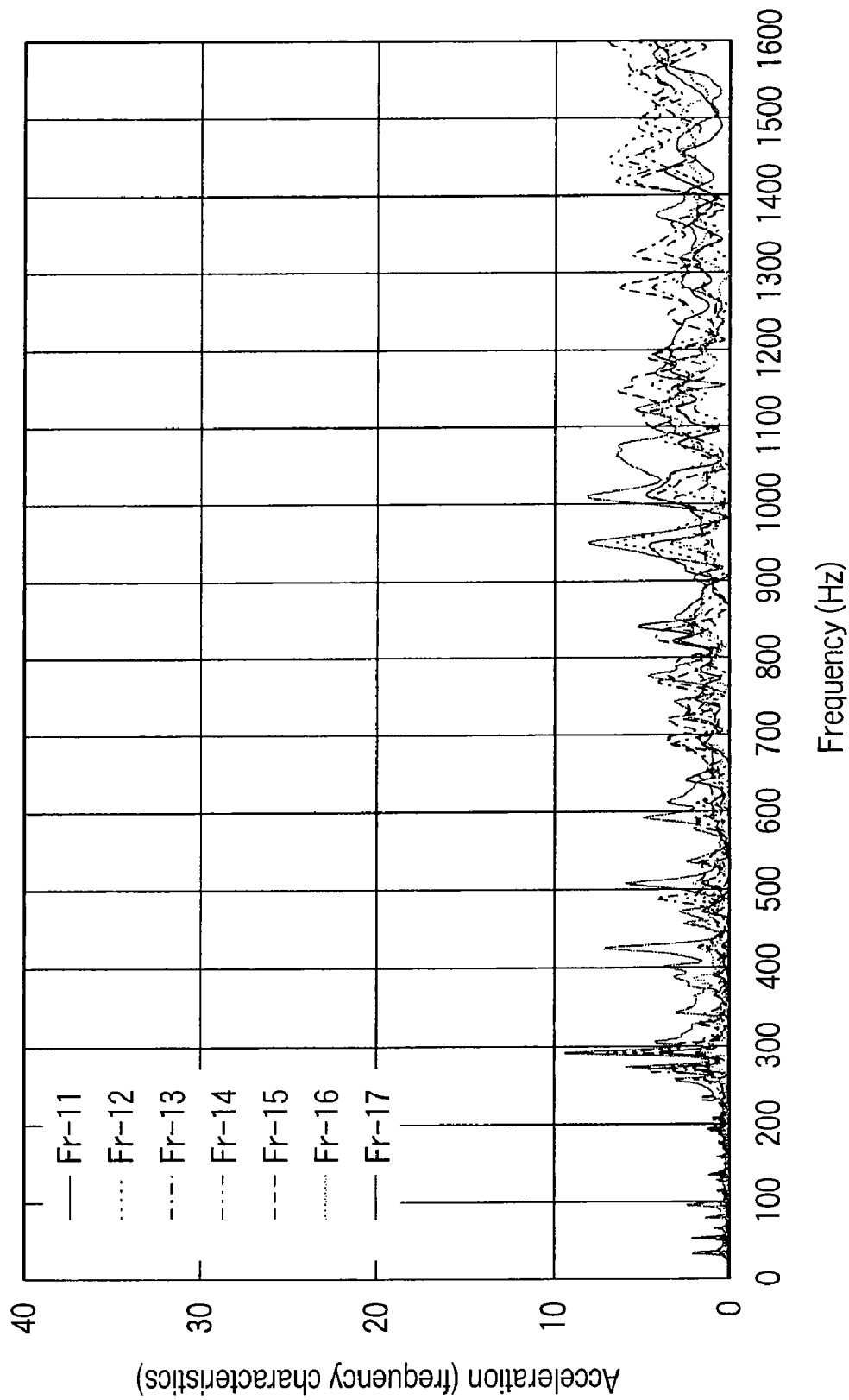
FIG. 18 is a graph showing the frequency characteristics of acceleration due to the vibration of the expanded cover portion of the medical X-ray CT apparatus according to the first embodiment.

FIG. 18 shows a result of a third experiment carried out when the expanded cover portion 11A is provided with two sets of curved members 61 as shown in FIG. 13 in the medical X-ray CT apparatus according to the first embodiment. However, the thickness of the expanded cover portion 11A is made identical with the reference case. In the third experiment, the vibration is particularly reduced in the high-frequency domain as compared with the second experiment. Further, in the third experiment, an increase in weight of the gantry cover 5 (part associated with maintenance/checkup including the expanded cover portion 11A) is restricted to about 10% as compared with the reference case.

Figure 19:
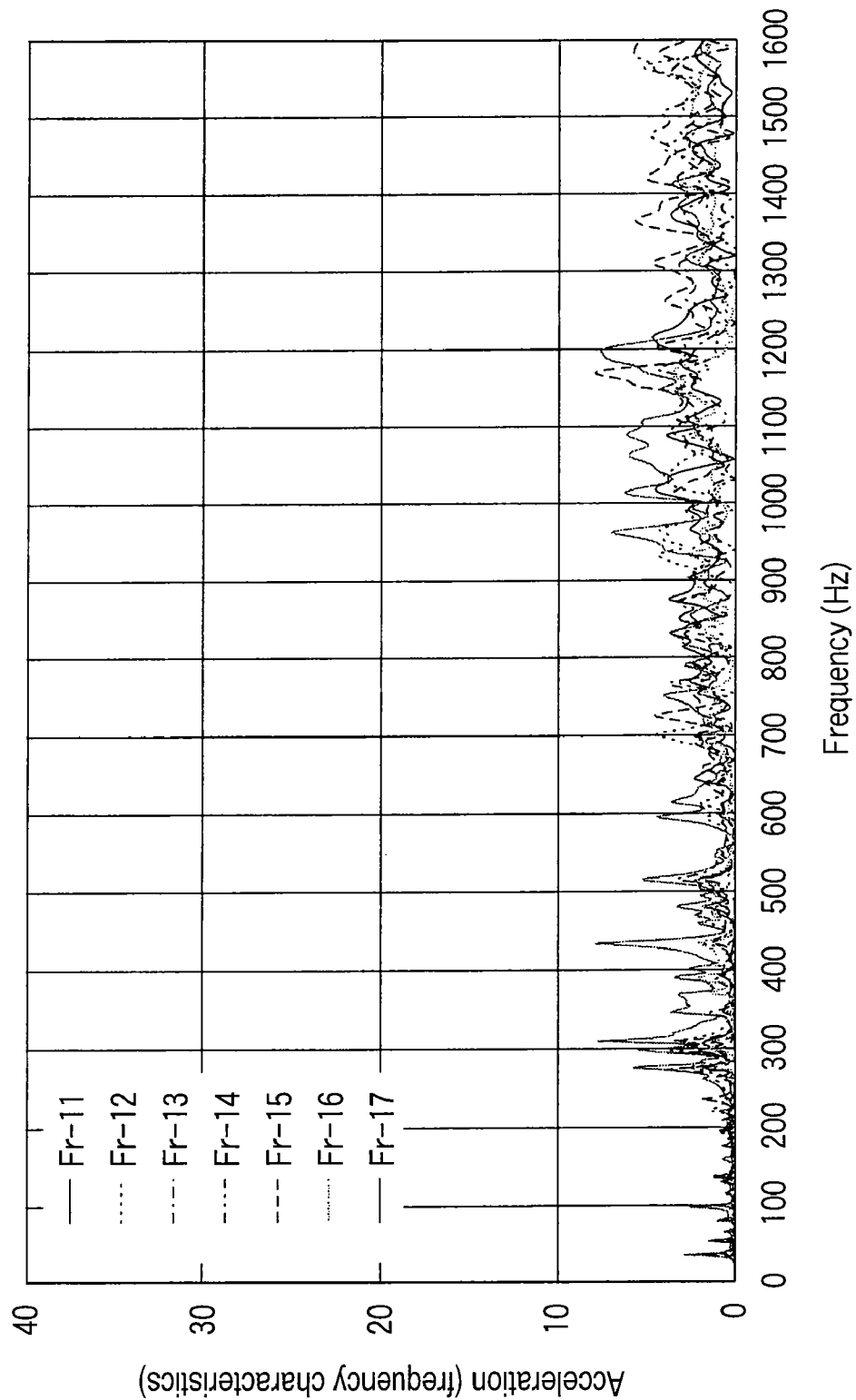
FIG. 19 is a graph showing the frequency characteristics of acceleration due to the vibration of the expanded cover portion of the medical X-ray CT apparatus according to the second embodiment.

FIG. 19 shows a result of a fourth experiment carried out when the expanded cover portion 11A is provided with two sets of curved members 61 as shown in FIG. 15 in the medical X-ray CT apparatus according to the second embodiment, the curved member 61 in the first set and the curved member 61 in the second set are connected by the connection members 63, and the first set of the curved members 61 farther from the rotational axis M than the second set are connected to the peripheral edge portion of the expanded cover portion 11A by the connection members 63 as shown in FIG. 14. However, the thickness of the expanded cover portion 11A is made identical with the reference case. In the fourth experiment, the vibration is particularly reduced in the frequency domain of 1400 to 1600 Hz as compared with the third experiment. Further, in the fourth experiment, an increase in weight of the gantry cover 5 (part associated with maintenance/checkup including the expanded cover portion 11A) is restricted to about 12% as compared with the reference case.

It is evident from the experimental results that it is possible to reduce the vibration of the expanded cover portion 11A in the medical X-ray CT apparatus according to the present invention without greatly increasing the weight of the gantry cover 5.

As described above, in the medical X-ray CT apparatus according to the present invention, the expanded cover portion 11A is provided with the curved members 61 corresponding to reinforcing members, the vibration of the expanded cover portion 11A due to the air pressure 13 produced by the rotation of the rotary portion 6 is reduced, and the vibration induced noise 14 produced from the expanded cover portion 11A is reduced.

In the medical X-ray CT apparatus of the present invention, it is possible to reduce the noise due to the vibration of the gantry cover at the time of tomography imaging while suppressing an increase in weight of the gantry cover, and securing the facility of the efficiency at the time of maintenance/checkup.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus for acquiring tomographic images of a patient, comprising:
    internal devices which include an X-ray source for irradiating the patient with X-rays, and an X-ray detector for detecting the X-rays transmitted through the patient and outputting an X-ray detection signal;
    a pedestal which has a rotary portion for mounting the internal devices and rotating the internal devices around the patient, and a support base supporting the rotary portion rotatably;
    a gantry cover, having exterior and interior surfaces, configured to cover the pedestal and to form a bore having an opening through which the patient is arranged in the bore, including an expanded cover portion which is so formed as to be expanded from the inner side of the bore toward the opening and to have a peripheral edge portion on the opening side; and
    at least one curved member, attached on the interior surface of the expanded cover portion, has first and second ends fixed to the peripheral edge portion, includes a curved portion curved convexly toward the inside of the bore with respect to a virtual straight line connecting the first and second ends, and is configured to be extended along a curved line segment which is obtained by geometrically projecting the virtual straight line onto the expanded cover portion.

2. The apparatus according to claim 1, wherein the pedestal has fixing parts which fix the gantry cover to the pedestal, and the one of the first and second ends is fixed to the fixing parts.

3. The apparatus according to claim 1, wherein the curved member is configured by reinforcing the material at the locations where the curved member is to be provided on the expanded cover portion.

4. The apparatus according to claim 1, further comprising connection members which are attached on the interior surface of the expanded cover portion, wherein each of the connection members is configured to connect the curved member and the peripheral edge portion to each other.

5. The apparatus according to claim 1, wherein the gantry cover is formed substantially symmetrical with respect to a certain reference plane.

6. The apparatus according to claim 5, further comprising a second curved member which is attached on the interior surface of the expanded cover portion, wherein the second curved member has other first and second ends fixed to the peripheral edge portion, includes a second curved portion curved convexly toward the inside of the bore with respect to a second virtual straight line connecting the other first and second ends to each other, and is configured to be extended along a second curved line segment which is obtained by geometrically projecting the second virtual straight line onto the expanded cover portion, wherein the first and second curved members are arranged substantially symmetrical to each other with respect to the reference plane.

7. The apparatus according to claim 6, further comprising connection members which are attached on the interior surface of the expanded cover portion, wherein each of the connection members is configured to connect the first curved member and the peripheral edge portion, and the second curved member and the peripheral edge portion to each other.

8. The apparatus according to claim 6, wherein the first and second curved members and the connection members are configured by reinforcing the material at the locations where the members are to be provided on the expanded cover portion.

* * * * *